United States Patent [19]
Russell et al.

[11] Patent Number: 6,103,468
[45] Date of Patent: *Aug. 15, 2000

[54] RAPID TWO-STAGE POLYMERASE CHAIN REACTION METHOD FOR DETECTION OF LACTIC ACID BACTERIA IN BEER

[75] Inventors: Inge Russell; Terrance M. Dowhanick; Robert J. Stewart, all of London, Canada

[73] Assignee: Labatt Brewing Company Limited, London, Canada

[*] Notice: This patent issued on a continued prosecution application filed under 37 CFR 1.53(d), and is subject to the twenty year patent term provisions of 35 U.S.C. 154(a)(2).

[21] Appl. No.: 08/944,974

[22] Filed: Oct. 7, 1997

[51] Int. Cl.$^7$ .............................. C12Q 1/68; C12P 19/34; C07H 21/04; G01N 33/53
[52] U.S. Cl. ................................ 435/6; 435/7.1; 435/7.2; 435/7.32; 435/15; 435/29; 435/91.2; 536/24.32; 536/24.33
[58] Field of Search .................................. 435/6, 7.1, 7.2, 435/7.32, 29, 91.1, 91.2, 91.5, 15; 536/24.3, 24.32, 24.33

[56] References Cited

U.S. PATENT DOCUMENTS

| | | | |
|---|---|---|---|
| 3,616,255 | 10/1971 | Nakagawa | 195/103.5 |
| 3,645,852 | 2/1972 | Axen et al. | 195/68 |
| 3,970,518 | 7/1976 | Giaever | 195/1.5 |
| 4,009,078 | 2/1977 | Wilkins et al. | 195/103.5 |
| 4,018,886 | 4/1977 | Giaever | 424/12 |
| 4,200,493 | 4/1980 | Wilkins et al. | 435/291 |
| 4,230,685 | 10/1980 | Senyei et al. | 424/12 |
| 4,246,343 | 1/1981 | Wilkins et al. | 435/32 |
| 4,267,234 | 5/1981 | Rembaum | 428/403 |
| 4,452,773 | 6/1984 | Molday | 424/1.1 |
| 4,554,088 | 11/1985 | Whitehead et al. | 252/62.54 |
| 4,582,788 | 4/1986 | Erlich | 435/6 |
| 4,659,678 | 4/1987 | Forrest et al. | 436/512 |
| 4,683,194 | 7/1987 | Saiki et al. | 435/6 |
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 4,855,045 | 8/1989 | Reed | 210/223 |
| 4,859,612 | 8/1989 | Cole et al. | 436/523 |
| 4,888,284 | 12/1989 | Konings et al. | 435/183 |
| 4,889,818 | 12/1989 | Gelfand et al. | 435/194 |
| 4,906,573 | 3/1990 | Barney et al. | 435/243 |
| 4,910,406 | 3/1990 | Craig et al. | 250/372 |
| 4,965,188 | 10/1990 | Mullis et al. | 435/6 |
| 5,075,216 | 12/1991 | Innis et al. | 435/6 |
| 5,079,352 | 1/1992 | Gelfand et al. | 536/27 |
| 5,116,736 | 5/1992 | Tahara et al. | 435/39 |
| 5,139,933 | 8/1992 | Green et al. | 435/732 |
| 5,314,809 | 5/1994 | Erlich et al. | 435/91.2 |
| 5,340,728 | 8/1994 | Grosz et al. | 435/91.2 |
| 5,395,498 | 3/1995 | Gombinsky et al. | 204/182.8 |
| 5,443,987 | 8/1995 | DeCicco et al. | 435/4 |
| 5,484,909 | 1/1996 | Nietupski et al. | 536/24.32 |
| 5,492,814 | 2/1996 | Weissleder | 435/725 |
| 5,506,130 | 4/1996 | Peterson et al. | 435/240.1 |
| 5,541,072 | 7/1996 | Wang et al. | 435/7.21 |
| 5,556,773 | 9/1996 | Youmo | 435/91.2 |
| 5,565,340 | 10/1996 | Chenchik et al. | 435/91.2 |
| 5,567,326 | 10/1996 | Ekenberg et al. | 210/695 |
| 5,571,674 | 11/1996 | Hoshina et al. | 435/6 |
| 5,578,467 | 11/1996 | Schuster et al. | 435/91.2 |
| 5,580,725 | 12/1996 | Klaenhammer et al. | 435/6 |

FOREIGN PATENT DOCUMENTS

| | | |
|---|---|---|
| 0 050 424 | 4/1982 | European Pat. Off. . |
| 0 084 796 A2 | 8/1983 | European Pat. Off. . |
| 0 200 362 A2 | 12/1986 | European Pat. Off. . |
| 0 201 184 A2 | 12/1986 | European Pat. Off. . |
| 0 237 362 A1 | 9/1987 | European Pat. Off. . |
| 0 258 017 A2 | 3/1988 | European Pat. Off. . |
| 0 469 610 A1 | 2/1992 | European Pat. Off. . |
| 0 200 362 B1 | 1/1993 | European Pat. Off. . |
| 6-141899 | 5/1994 | Japan . |
| 7-289295 | 11/1995 | Japan . |

OTHER PUBLICATIONS

Robert J. Stewart and Terrance M. Dowhanick, "Rapid Detection of Lactic Acid in Fermenter Samples Using a Nested Polymerase Chain Reaction," J. Amer. Soc. Brew. Chem. 54(2): 78–84 (Apr. 1996).

Pär–Gunnar Lantz, Bärbel Hahn–Hägerdal, and Peter Rådström, "Sample preparation methods in PCR–based detection of food pathogens," in Trends in Food Science & Technology, Dec. 1994 (vol. 5), pp. 384–389.

Dowhanick, T.M. Advances in yeast and contaminant determination: the future of the so called 'rapid' methods. Cerevisia 20(4):40–50., 1995.

Tsuchiya, Y. et al. Detection of beer spoilage organisms by polymerase chain reaciton technology. J. Amer. Soc. Brew. Chem. 50(2):64–67., 1992.

DiMichele, L. et al. Rapid, species–specific detection of lactic acid bacteria from beer using the polymerase chain reaction. J. Amer. Soc. Brew. Chem. 51:63–66., 1993.

Yasui, T. et al. Can. J. Microbiol. 43(2):157–163., Feb. 1997.
Satokari, R. et al. Int. J. Food Microbiol. 45(2):119–127., Dec. 1998.

Primary Examiner—Carla J. Myers
Assistant Examiner—Diana Johannsen
Attorney, Agent, or Firm—Levy & Grandinetti

[57] ABSTRACT

A method for the rapid, high-sensitivity detection of bacteria in a malt beverage comprising liquid and solid components, wherein the method comprises the steps of:

aseptically sampling said malt beverage;

separating the solids in the sample from the liquid by means of a substrate having antibodies attached thereto;

extracting DNA from the separated solids;

subjecting the extracted DNA to a nested polymerase chain reaction, said reaction comprising:

enzymatically amplifying at least one fragment of said extracted DNA using at least one highly conserved primer to produce a first amplified sample;

enzymatically amplifying a product sequence from said first amplified sample, using a less highly conserved primer to produce a second amplified sample;

examining said second amplified sample for the presence of DNA fragments associated with said bacteria.

12 Claims, No Drawings

RAPID TWO-STAGE POLYMERASE CHAIN REACTION METHOD FOR DETECTION OF LACTIC ACID BACTERIA IN BEER

BACKGROUND OF THE INVENTION

1. Field of the Invention

The present invention relates to the rapid, high-sensitivity detection of bacterial contamination in malt beverages and, in particular, to a nested polymerase chain reaction method for the amplified detection of nucleic acid sequences associated with lactic acid bacterial contamination in such beverages.

2. Description of Related Art

The process of preparing fermented malt beverages, such as, beer, ale, porter, malt liquor, and other similar fermented alcoholic beverages, hereinafter referred to simply as "beer" for convenience, is historically well established. As practiced in modern breweries, the process, in brief, comprises preparing a "mash" of malt, usually with cereal adjuncts, and heating the mash to solubilize the proteins and convert the starch into sugar and dextrins. The insoluble grains are filtered off and washed with hot water that is then combined with the soluble material. The resulting wort is boiled in a brew kettle to inactivate enzymes, sterilize the wort, extract desired hop components from added hops, and coagulate certain protein-like substances. The wort is then strained to remove spent hops and coagulum, cooled, pitched with yeast, and fermented. The fermented brew, known as "green" or "ruh" beer, is then aged ("lagered") and clarified, filtered, and carbonated to produce the desired finished beer.

During the brewing process, the brewer must constantly be on guard against contamination by bacteria that can spoil the beer. A number of methods have been devised over the years to detect these bacteria, but, until recently, these methods were laborious and time-consuming, adding to the manufacturing cost.

For example, traditional methods for detecting the presence of bacteria in comestibles require an incubation period to allow for recovery of injured bacteria, growth of these bacteria from a background of competing microorganisms, and an increase in bacterial cell numbers to more readily aid in identification. More than one incubation may be needed.

These conventional methods are slow, requiring 5 to 14 days or more, depending upon the bacteria species of interest, and may be inaccurate, providing false negatives.

Barney et al. (*Tech. Q. Master Brew Assoc. Am.* 29(3):91–95 (1992)) discuss the difficulties attendant the detection of slow-growing beer spoilage microorganisms, which require fairly specific conditions to support detectable growth using classical culturing techniques.

The same article, however, also points out that direct detection techniques that do not depend on culturing (for example, direct epifluorescence technique (DEFT), PCR techniques, or flow cytometry) are susceptible to interference, which causes high error rates; are labor intensive; and are difficult to automate.

Also discussed are the so-called "rapid" indirect detection methods, which require three to five days using the impedance/conductance method, spectrophotometry, or metabolite detection, or two to three days using ATP bioluminescence.

In general, the article explores the shortfalls of each of the available methodologies and emphasizes the need for improved, rapid detection methods for dealing with beer spoilage microorganisms.

New biological methods, some of which involve the polymerase chain reaction (PCR), have contributed significantly to improving the accuracy of the assay and reducing the time required to obtain useful results.

PCR is a process for amplifying nucleic acids so as to improve the sensitivity and specificity of their detection. It involves the use of two oligonucleotide primers, a polymerization agent, a target nucleic acid template, and successive cycles of denaturation of nucleic acid, annealing, and extension of the primers to produce a large number of copies of a particular nucleic acid segment. With this method, segments of single copy genomic DNA can be amplified to more than 10 million.

U.S. Pat. Nos. 4,683,195 and 4,683,202 disclose the process as:

(1) denaturing DNA template strands at elevated temperature;

(2) annealing oligonucleotide primers to the DNA templates at the 3' ends of the sequence of interest at hybridization temperature; and (3) extending the 3' ends of the primer with nucleotide triphosphates in the presence of a thermostable DNA polymerase, whereby the desired template sequence is replicated.

Steps 1 to 3 are then repeated cyclically, with the primer extension products of one cycle becoming the templates for the next.

U.S. Pat. No. 4,683,202 also discloses a nested PCR method in which a second set of primers is used to amplify a smaller DNA sequence contained within the DNA sequence amplified by the first primer set. These nested or inner primers will flank the target nucleic acid. The term "flanking primers" is used to describe primers that are complementary to segments on the 3' end portions of the double-stranded nucleic acid segment that is polymerized and amplified during the PCR process.

U.S. Pat. No. 4,965,188 discloses a process for amplifying any target nucleic acid sequence contained in a nucleic acid or mixture thereof that comprises treating separate complementary strands of the nucleic acid with a molar excess of two oligonucleotide primers and extending the primers with a thermostable enzyme to form complementary primer extension products that act as templates for synthesizing the desired nucleic acid sequence. The amplified sequence is said to be readily detectable. The steps of the reaction can be repeated as often as desired and involve temperature cycling to effect hybridization, promotion of activity of the enzyme, and denaturation of the hybrids formed.

U.S. Pat. No. 5,075,216 discloses that dideoxynucleotide DNA sequencing methods can be improved by utilizing the DNA polymerase from *Thermus aquaticus* (Taq) to catalyze the primer extension reactions.

U.S. Pat. No. 5,079,352 discloses recombinant DNA vectors that encode a thermostable DNA polymerase and are said to be useful in the recombinant production of thermostable DNA polymerase. The recombinant thermostable polymerase is preferred for use in the production of DNA in a polymerase chain reaction. Especially useful vectors encode the about 94,000 dalton thermostable DNA polymerase from *Thermus aquaticus*.

U.S. Pat. No. 5,139,933 discloses an assay method to quickly detect the presence of Listeria strains in samples, characterized by the use of antibodies to selectively capture the peptidoglycan and teichoic acid components of the listeriae bacterial cell wall.

U.S. Pat. No. 5,314,809 discloses methods for enhanced specificity and sensitivity of nucleic acid amplification. The methods are simplified nested amplification procedures wherein both inner and outer primer pairs are present in the amplification reaction mixture. According to the methods, the thermocycling profile, as well as the sequences, length, and concentration of amplification primers, are modified to regulate which primers are annealed and extended on the target during any particular amplification cycle.

U.S. Pat. No. 5,340,728 discloses an improved method for performing a nested PCR amplification of a target piece of DNA, wherein by controlling the annealing times and concentration of both the outer and the inner set of primers, highly specific and efficient amplification of a targeted piece of DNA can be achieved within one reaction vessel without depletion or removal of the outer primers from the reaction mixture vessel.

U.S. Pat. No. 5,556,773 discloses a nested polymerase chain reaction performed in a single reaction tube that remains closed after the reaction mixtures for each amplification have been introduced therein. The reaction mixture for the second PCR amplification is sequestered and preserved in an upper portion of the single, closed reaction tube during the first amplification, and subsequently introduced into the reaction space containing the end product of the first PCR amplification, without opening the reaction tube.

EP 200362 and EP 201184 disclose a process for amplifying and detecting any target nucleic acid sequence contained in a nucleic acid or mixture thereof. The process comprises treating separate complementary strands of the nucleic acid with a molar excess of two oligonucleotide primers, extending the primers to form complementary primer extension products that act as templates for synthesizing the desired nucleic acid sequence, and detecting the sequence so amplified. The steps of the reaction may be carried out stepwise or simultaneously and can be repeated as often as desired.

In addition, a specific nucleic acid sequence may be cloned into a vector by using primers to amplify the sequence, which contain restriction sites on their non-complementary ends, and a nucleic acid fragment may be prepared from an existing shorter fragment using the amplification process.

EP 258017 discloses a purified enzyme having unique characteristics. Preferably, it is isolated from the *Thermus aquaticus* species and has a molecular weight of about 86,000 to 90,000 daltons. The thermostable enzyme may be native or recombinant and may be used in a temperature-cycling chain reaction wherein at least one nucleic acid sequence is amplified in quantity from an existing sequence with the aid of selected primers and nucleotide triphosphates. The amplification process comprises treating separate complementary strands of the nucleic acid with a molar excess of two oligonucleotide primers, extending the primers with a thermostable enzyme to form complementary primer extension products which act as templates for synthesizing the desired nucleic acid sequence, and detecting the sequence so amplified. The steps of the reaction can be repeated as often as desired and involve temperature cycling to effect hybridization, promotion of activity of the enzyme, and denaturation of the hybrids formed. The enzyme is preferably stored in a buffer of nonionic detergents that lends stability to the enzyme.

The use of polymerase chain reaction methodologies in the detection of beer spoilage infections is also known in the art. For example, in *J. Am. Soc. Brew. Chem.* 51(1):40–41 (1993) (see also, *J. Am. Soc. Brew. Chem.* 50(2):64–67 (1992)), there is disclosed a method for detecting the beer spoilage microorganism *Lactobacillus brevis,* in particular, using a polymerase chain reaction technique. The method requires that the sample be filtered through a submicron filter, after which the filter is ultrasonicated in an ethanol bath in order to improve the release of cells from the filter substrate. Transfer RNA (tRNA) is added to the ethanol to coprecipitate the extracted DNA and a Pfu polymerase is used in the PCR amplification process, whereby the detection limit is lowered from 30 cells to 9 cells per 250 mL of beer sample.

Japanese published application number 6141899 details a process for the highly sensitive detection of lactic acid bacteria, *L. brevis* in particular, as follows:

(1) filtering the infected beer sample through a polycarbonate membrane filter;

(2) ultrasonicating the filter in a volatile solvent solution;

(3) isolating the lactic acid bacteria from the filter and evaporating the volatile solvent;

(4) treating the residual lactic acid bacteria-containing sample with lysozyme, mutanolysin, proteinase K, and SDS to extract DNA from that sample;

(5) using tRNA coprecipitant to precipitate DNA from the sample, after it has been resuspended in ethanol;

(6) then, finally, applying the polymerase chain reaction to the DNA precipitate using either of two selected oligonucleotides (or one of their respective complements):

5'-TGTGGTGGCGATAGCCTGAA-3' (SEQ ID NO:1) or
5'-GCGTGGCAACGTCCTATCCT-3' (SEQ ID NO:2).

The detection time is reportedly reduced to about 11 hours.

DiMichele et al. (*J. Am. Soc. Brew. Chem.* 51(2):63–66 (1993)) disclose a more rapid technique that could be carried out in about six hours. However, that technique was species specific and had a detection threshold of about 20 cells per mL in beer. The process depended on sample filtration and dissolution, followed by PCR amplification and gel electrophoresis of certain species specific regions of the 16S rRNA. While the elapsed time for the detection was reduced to six hours, samples had to be carried out in parallel for each of a predetermined number of species (for example, for *L. brevis, L. casei,* and *L. plantarum*), which makes the method very labor intensive and, hence, costly.

U.S. Pat. No. 5,484,909 discloses nucleic acid sequences that preferentially bind to the rRNA or rDNA of microorganisms that cause the spoilage of beer. The beer spoilage microorganisms are predominantly of the genera Lactobacillus and Pediococcus. The nucleic acids can be used as probes in assays to detect the presence of these microorganisms. In practice, a sample, such as a swab or liquid aliquot is processed to liberate the total nucleic acid content. The sample, putatively containing disrupted beer-spoilage organisms, is incubated in the presence of a capture probe, detector probe, and magnetic particle beads, which have been derivatized with oligo-deoxy Thymidine in chaotropic buffer such as guanidine isothiocyanate.

If target molecules (beer-spoilage microorganisms of the genus Pediococcus or Lactobacillus) are present, a Bead-Capture Probe-Target-Detector Probe hybridization complex is formed. The presence of a magnet near the bottom of the reaction tube will cause the magnetic particle-hybridization complex to adhere to the side of the tube, enabling the removal of the sample matrix, unbound probe, and other constituents not hybridized.

In *Advances in Detection and Identification Methods Applicable to the Brewing Industry,* in BEER AND WINE PRODUCTION (ACS Symp. Ser. 536) 13–30 (B. P. Gump ed. 1993), Dowhanick and Russell survey contemporaneous developments in techniques that are potentially useful for the detection and identification of beer spoilage microorganisms. Impedimetric detection, ATP bioluminescence, protein characterization using polyacrylamide gel electrophoresis, immunological analysis, DNA probe hybridization, karyotyping using pulsed field gel electrophoresis, are all discussed. In addition, the paper deals with DNA sequence amplification using PCR either with specifically designed probes or nonspecific "random amplified polymorphic DNA probes." While all of the described methodologies are recognized as being much faster than conventional microbiological analyses that are based on culturing and microscopic examination, they are not generally practical for routine quality control purposes.

Stewart et al. (*J. Am. Soc. Brewing Chemists* 54(2):78–84 (1996)) disclose a nested PCR protocol that greatly improves the sensitivity of detection of lactic acid bacteria in the presence of a high concentration of interfering substances, such as yeast cells in a fermenter sample. By using the 16S-rDNA genes as targets for PCR amplification, they taught that primers could be designed to react with a family of lactic acid bacteria that are potential beer spoiling organisms, but do not react with other nonspoilage organisms. This is possible because the rDNA contains both highly conserved sequences to all bacterial species as well as highly variable regions that are unique to individual species or families of species. The sensitivity of detection is very high, allowing application of the nested PCR protocol to the screening of samples of fermenting yeast for the presence of lactic acid bacteria. The short time required to complete the assay (six hours) allows the monitoring of yeast later in fermentation, thereby allowing an improved assessment of contamination by lactic acid bacteria. The disclosure of this article is incorporated herein by reference.

It is clear that there remains a need in the brewing arts for an efficacious method for rapidly detecting bacterial infections.

SUMMARY OF THE INVENTION

In accordance with a broad aspect of the present invention, there is provided a method for the rapid, high-sensitivity detection of bacterial contamination in malt beverages. In a preferred aspect of the present invention, there is provided a method for the rapid, high-sensitivity detection of bacterial contamination in finished beer samples.

The method, in general, comprises separation by means of a substrate having antibodies attached thereto, coupled with a nested polymerase chain reaction method for amplified detection of nucleic acid sequences associated with the bacterial contamination in the brewing process.

More particularly, the present invention is directed to a method for the rapid, high-sensitivity detection of bacteria in a malt beverage comprising liquid and solid components, wherein the method comprises the steps of:

aseptically sampling said malt beverage;

separating the solids in the sample from the liquid by means of a substrate having antibodies attached thereto;

extracting DNA from the separated solids;

subjecting the extracted DNA to a nested polymerase chain reaction, said reaction comprising:

enzymatically amplifying at least one fragment of said extracted DNA using at least one highly conserved primer to produce a first amplified sample; and enzymatically amplifying a product sequence from said first amplified sample, using at least one less highly conserved primer to produce a second amplified sample; and then examining said second amplified sample for the presence of DNA fragments associated with said bacteria.

Those skilled in the art will understand that each of the amplification steps of the nested polymerase chain reaction can be repeated as many times as may be desired. The terms "first amplified sample" and "second amplified sample" as used herein are intended to refer to the final products after the first round of amplifications and the second round of amplifications, respectively.

In a particularly preferred aspect, the present invention is directed to a method for the rapid, high-sensitivity detection of lactic acid bacteria in a finished beer sample, wherein the method comprises the steps of:

aseptically sampling a finished beer;

separating any bacteria in the sample by means of beads having antibodies attached thereto;

extracting DNA from the separated bacteria;

subjecting the extracted DNA to a nested polymerase chain reaction, said reaction comprising:

enzymatically amplifying a universal fragment of bacterial 16S rDNA under relatively inefficient conditions using a pair of 16S rDNA specific primers to produce a first amplified sample; and further enzymatically amplifying a product sequence from said first amplified sample using a pair of lactic acid bacteria specific primers to produce efficiently a second amplified sample; and then subjecting the second amplified sample to separation and staining to detectably segregate an identifiable 750 bp band.

In an especially preferred form of the present invention, the separation of the second amplified sample is accomplished with gel electrophoresis, followed by ethidium bromide staining. Under UV light, it is possible to detect an identifiable 750 bp (i.e., double stranded base pairs) band, if the original sample contained lactic acid bacterial contamination.

The amplified product can also be labelled using nucleotides in the PCR reaction buffer that are prelabelled with radioactive isotopes or chromogenic, fluorescent, or chemiluminescent substituents. These labels can also be used in conjunction with electrophoretic or chromatographic techniques. Other separation and detection (for example, staining) techniques can also be employed, if desired.

It will be understood that the term "lactic acid bacteria," as used herein, refers to bacteria that are capable of producing lactic acid.

DESCRIPTION OF THE PREFERRED EMBODIMENTS

As mentioned above, the present invention is directed to a method for the rapid, high-sensitivity detection of bacteria in a malt beverage comprising liquid and solid components, wherein the method comprises the steps of:

aseptically sampling said malt beverage;

separating the solids in the sample from the liquid by means of a substrate, preferably beads, having antibodies attached thereto;

extracting DNA from the separated solids;

subjecting the extracted DNA to a nested polymerase chain reaction, said reaction comprising:

enzymatically amplifying at least one fragment of said extracted DNA using at least one highly conserved primer to produce a first amplified sample; and enzymatically amplifying a product sequence from said first amplified sample, using at least one less highly conserved primer to produce a second amplified sample; and then examining said second amplified sample for the presence of DNA fragments associated with said bacteria.

As employed herein, the term "malt beverage" is intended to include not only the finished product of the brewing process, but also any and all of its precursors in the process. Use of the process of the invention will, however, find its greatest usefulness with finished beer and this aspect of the invention is therefore preferred.

The aseptic sampling step of the process of the present invention can be carried out by any conventional sampling method and/or means well known to those skilled in the art.

For the separation step, lactic acid bacteria antibodies, which are attached to a suitable substrate, preferably finely divided particles or beads, are employed. In a preferred embodiment of the present invention, a substrate in the form of magnetic particles is used to facilitate the separation step.

Magnetic particles are well known in the art, as is their use in immune and other biospecific affinity reactions. See, for example, U.S. Pat. No. 4,554,088 and IMMUNOASSAYS FOR CLINICAL CHEMISTRY 147–62 (Hunter et al. eds. 1983).

Magnetic particles are advantageous in that they can be coated with biofunctional polymers, for example, proteins, provide very high surface areas, and give reasonable reaction kinetics. Particles that range in size from 0.7 to 1.5 microns and that provide useful solid supports for immunologic reagents have been described in, for example, U.S. Pat. Nos. 3,970,518; 4,018,886; 4,230,685; 4,267,234; 4,452,773; 4,554,088; and 4,659,678.

These particles can be considered as being classifiable into one or the other of two major categories:

(1) Those that are permanently magnetizable, or ferromagnetic; and (2) Those that demonstrate bulk magnetic behavior only when subjected to a magnetic field, generally referred to as magnetically responsive particles or superparamagnetic particles.

Particles belonging to either category can be employed in the practice of the present invention, although those of category 1 are preferred.

Thus, in a preferred form of the invention, the antibodies are immobilized on magnetic particles. This can be done by methods known in the art; see, for example, U.S. Pat. Nos. 3,970,518; 4,018,886; 4,855,045; and 4,230,685. The antibodies can, if desired, be attached to the magnetic particles through a protein intermediate, for example, Protein A. In this method, the protein is first attached to the magnetic particles and the antibodies are then bound to the protein. The use of Protein A can enhance the effectiveness of capture by the attached antibodies (Forsgren et al., *J. Immunol.* 99:19 (1977)). It attaches to the Fc portion of IgG subclass antibodies, thus extending and presenting the Fab portion of these antibodies. The resulting correct orientation of the antibodies and extension away from the particles leads to a very effective interaction between the bound antibodies and their target.

Proteins can be attached to the magnetic particles by any of several processes known to those skilled in the art. For example, magnetic iron oxide particles about one $\mu$m in diameter can be reacted first with 3-aminopropyltriethoxysilane, then with glutaraldehyde, and then mixed with, for example, Protein A to form a covalent bond therewith. Antibodies are then added and, after a short incubation period, complexes form (H. H. Weetall, *Meth. in Enzymol.* 44:134–48 (1976)) that are ready for use in bacterial cell capture.

In the practice of the present invention, the preferred immobilizing substrate for the capturing antibodies is magnetic particles, i.e., magnetic beads. However, the use of polyacrylamide beads or other similar substrates for immobilizing antibodies is also feasible. These other substrates include beads of agarose or other polysaccharides, cross-linked dextrans, glass beads, latex beads, glass fiber filters, cellulose nitrate filters, nylon filters, and the like. Methods to bind antibodies to polyacrylamide beads and other matrices are well known to those skilled in the art. For example, carbodiimides can be used to couple antibodies to polyacrylamide beads (see J. Bauminger, et al., *Methods of Enzymology*, 70:151–59 (1980)). U.S. Pat. No. 3,645,852 discloses another method involving binding biopolymers to polysaccharides.

The immobilized antibodies can then be used to capture and immobilize the bacterial antigens and thereby separate them from the malt beverage.

The antibodies employed can be either polyclonal or monoclonal. If it is desired to employ polyclonal antibodies, their preparation can be carried out by methods known in the art, for example, such as those described by B. A. Hurn et al. in *Meth. in Enzymology* 104–42 (H. Van Vurakis and J. Langone ed. 1980).

If it is desired to employ monoclonal antibodies, their preparation can also be carried out by methods known in the art (see, for example, Milstein et al., *Nature* 256:495–97 (1975)). In a typical process, an animal is injected with an immunogen. After allowing time for the animal to produce antibodies to the immunogen, it is killed. Cells are then removed and fused with myeloma cells, yielding hybridoma cells that can reproduce in vitro. Each cell so produced can then express genetic information for one specific antibody, which will only recognize a single antigenic determinant of the immunogen.

Cells cultured from individual hybridoma cells are then screened to determine which antibodies have the highest affinity for the target antigen, the greatest stability to the assay conditions, and the least cross reactivity to possible contaminating antigens.

As indicated above, it is preferred in the practice of the present invention to employ magnetic beads as the substrate for the antibodies that capture the bacterial cells. However, other methods are feasible, including affinity column chromatography or using suspended beads in liquefied samples to capture the targets, followed by centrifugation to concentrate the target cells or antigens. Additionally, target cells or antigens can be collected on sticks that are coated with immobilized antibodies and stirred through liquid samples. In another alternative, the bacterial sample can be filtered through a membrane coated with the antibodies.

The use of other ligands, such as, lectins (for example, Concanavalin A), that can bind to bacteria can also be used with magnetic particles. That is, any compound that can be shown to bind selectively to the lactic acid bacteria can, conceivably, be used as an agent to capture the intact bacteria using this technique. In addition, cells that bind selectively to lactic acid bacteria can also be utilized in place of, or in concert with, the coated magnetic particles. For example, a hybridoma cell that produces cell surface antibodies to acid bacteria or a collective of different hybridomata that express antibodies to the three principal genera of lactic acid bacteria can be used as an absorbent for lactic acid bacteria. Furthermore, the ligand used to capture the bacteria need not be specific to lactic acid bacteria. It could capture all types of bacteria, or only gram positive bacteria, for example. This is possible not only because the bacterial contamination of the brewing process is generally restricted to lactic acid bacteria, but the specificity of the detection method is obtained using the nested PCR reaction. The presence of excess nonlactic acid bacterial DNA does not interfere with the reaction.

Once separated from the malt beverage sample, the bacterial cells are then lysed and the DNA therefrom is extracted by means known to those skilled in the art and subjected to a nested polymerase chain reaction to significantly amplify the amount of it available for analysis.

PCR amplification of DNA involves repeated cycles of heat-denaturing the DNA, annealing two oligonucleotide primers to sequences that flank the DNA segment to be amplified, and extending the annealed primers with a DNA polymerase. The primers hybridize to opposite strands of the target sequence and are oriented so that DNA synthesis by the polymerase proceeds across the region between the primers, effectively doubling the amount of the DNA segment. Moreover, because the extension products are also complementary to and capable of binding primers, each successive cycle essentially doubles the amount of DNA synthesized in the previous cycle.

"Primer" means a natural or synthetic oligonucleotide that acts as a point of initiation for the synthesis of an extension product complementary to a given nucleic acid strand. The synthesis is carried out in the presence of the four different nucleoside triphosphates, a DNA polymerase, and an appropriate buffer at a suitable temperature. A primer must be sufficiently complementary to anneal to the nucleic acid template under the reaction conditions, but it is not necessary for every nucleotide of the primer to anneal for primer extension to occur and its sequence does not have to be exactly the same as the sequence of the template.

"Oligonucleotide" means a molecule having at least two deoxyribonucleotides or ribonucleotides. It is preferred that there be at least three, and, more preferably, at least ten deoxyribonucleotides or ribonucleotides. These molecules can be prepared by cloning or by synthetic means known in the art (see, for example, Matteucci et al., *J. Am. Chem. Soc.* 103:3185–91 (1981)). Apparatus for the automated synthesis of oligonucleotides is also commercially available.

The DNA polymerase can, for example, be Taq polymerase, which is a thermostable polymerase that is active at high temperatures. Methods for the preparation of Taq are disclosed in U.S. Pat. No. 4,889,818. Taq polymerase is available from Perkin-Elmer Cetus Instruments as a recombinant product or purified from *Thermus aquaticus*. However, other thermostable DNA polymerases isolated from Thermus species or non-Thermus species (for example, *Thermus thermophilous* or *Thermotoga maritima*), as well as nonthermostable DNA polymerase such as T4 DNA polymerase, T7 DNA polymerase, *E. coli* DNA polymerase I, or the Klenow fragment of *E. coli* can be used in PCR. The nucleic-5'-triphosphates utilized in the extension process, typically dATP, dCTP, dGTP, and dTTP, are present in a total concentration typically ranging from 400 μM to 4.0 mM during the extension reaction, although the concentration is preferably between 500 μM and 1.5 mM.

Conventional PCR is adequate for the detection of nucleic acid sequences when the source material is derived from hundreds or thousands of cells. However, rare target sequences may be indeterminate or undetectable when the conventional process is used. To ameliorate this problem, nested PCR procedures have been developed, whereby the amplifying power of the process is increased and the detection sensitivity is enhanced.

As is known in the art, nested PCR procedures include a first amplification process comprising amplifying an extended target sequence and a second, subsequent, amplification process comprising amplifying an internal sequence from the product of the first amplification process. The internal sequence may or may not overlap one of the ends of the extended sequence. The first amplification process employs a pair of outer primers and the second amplification process employs a pair of inner primers. For effective nested amplification, it is necessary to terminate the amplification of the outer primer set after the first stage to allow the inner primers alone to amplify the DNA in the second stage. To minimize the carryover of outer primer into the second stage, the first stage product has traditionally been diluted (E. Rimstad et al., *J. Clin. Microbiol.* 28:2275 (1990)) or only a small fraction of it (2 to 10 percent) is added to the second stage reaction (D. Welch et al., *Appl. Env. Microbiol.* 56:2494 (1990)).

In the practice of the present invention, a nested polymerase chain reaction is used for the amplified detection of the nucleic acid sequences of the bacteria that are associated with the undesirable production of lactic acid. More particularly, species of bacteria that are detected by way of the following PCR reaction using the primers LP1 (5'-GCG GCG TGC CTA ATA CAT GC-3') (SEQ ID NO:3) and C (5'-TCA GTT ACA GAC CAG AC-3') (SEQ ID NO:4) include the following:

*Pediococcus damnosus;*
*Lactobacillus brevis (varlindneri);*
*Lactobacillus plantarum;*
*Pediococcus damnosus (cerevisiae);*
*Lactobacillus acidophilus;*
*Lactobacillus bulgaricus;*
*Leuconostoc mesenteroides;*
*Lactobacillus helveticus;*
*Pediococcus inopinatus;*
*Lactobacillus fermentum;*
*Lactobacillus casei alactosus;*
*Pediococcus halophilus;*
*Lactobacillus delbrueckii;*
*Leuconostoc mesenteroides* subsp. *dextrinicum;*
*Lactobacillus buchneri;*
*Lactobacillus casei varcasei;*
*Pediococcus intermedius;*
*Pediococcus parvulus;*
*Pediococcus dextrinicus;*
*Streptococcus lactis.*

In addition, a number of, as yet, specifically unidentified members of Lactobacillus genera have been found to be reactive.

The primary bacterial strains capable of spoiling beer are known in the art. They are, in decreasing order of importance: *Lactobacillus brevis, Pediococcus damnosus, L. casei, L. lindneri, L. coryniformis, L. buchneri, L. plantarum,* and *L. curvatus.*

Species that are not detected using the primers called for in the following procedures are as follows: *Streptococcus durans, Escherichia coli, Kluyvera ascorbata, Pseudomonas fluorescens,* Acetobacter spp., *Klebsiella pneumoniae, Enterobacter cloacae, Obesumbacterium proteus, Clostridium beijinickii, Pectinatus cerevisuiphilus, Pectinatus frisingensis, Klebsiella pneumoniae, Escherichia adecarboxylata, Bacillus subtilitis, Acetobacter liquefaciens,* Megasphaera spp., *Micrococcus luteus, Zymomonas mobilis, Serratus oderifera, Obesumbacterium proteus, Streptococcus salivarus, Streptococcus faecalis,* Gluconobacter, *Bacillus pumilis, Acetobacter aceti,* and *Enterobacter aerogenes.*

A preferred method of the present invention includes the steps of aseptically sampling a malt beverage, preferably, a finished beer, separating the solids in the sample from the liquid by means of beads having antibodies attached thereto, and extracting DNA from the separated solids.

Then the extracted DNA is subjected to a nested polymerase chain reaction process comprising amplifying a universal fragment of bacterial 16S rDNA under relatively inefficient conditions using either or both of a pair of 16S rDNA specific primers to produce an enzymatically amplified sample; and then further enzymatically amplifying a product sequence from the amplified sample using one or more specific (i.e., lower conservancy) lactic acid bacteria primers to amplify efficiently (i.e., more specifically) the DNA sequences associated with the lactic acid bacterial contamination to produce a derivative amplified sample.

The specifically preferred practice of the amplification aspect of the process of the present invention is outlined below:

The reactions are performed in sterile 0.5 mL microcentrifuge tubes. Each tube contains a 50 microliter reaction volume overlaid with 50 microliters of sterile light paraffin oil. Thermocycling is achieved using either a PTC-100 Thermocycler (M J Research Inc.) or Biometra Trio Thermocycler (Biometra Inc.).

First Round

The final 50 microliter volume contains the following reagents: 10 millimolar Tris-HCl, pH 8.30; 1.5 millimolar magnesium chloride; 50 millimolar potassium chloride; 1.25 units of Taq DNA polymerase (Boehringer Mannheim); and 100 micromolar of each deoxynucleotide: dATP (deoxyadenosine triphosphate), dTTP (deoxythymidine triphosphate), dGTP (deoxyguanidine triphosphate), and dCTP (deoxycytosine triphosphate). The thermostable Taq DNA polymerase is added from a concentrated solution provided by the manufacturer which contains 20 millimolar Tris-HCl, 1 millimolar dithiothreitol, 0.1 millimolar EDTA, 0.1 molar potassium chloride, 0.5 percent (v/v) Nonidet®, 0.5 percent (v/v) Tween® 20, and 50 percent (v/v) glycerol, pH 8.0. The enzyme is diluted by a factor of 1/200 (v/v) and the effect of these reagents on the final reagent concentrations is negligible. The concentrations of both of the primers NSN10F (5'-AGA GTT TGA TCC TGG CTG AGC-3') (SEQ ID NO:5) and NSN986R (5'-TGC TCC ACC CGT TGT GCG-3') (SEQ ID NO:6) in the reaction mixture is 50 nanomoles/liter. The reagents are made up in an initial volume of 40 microliters and the 50 microliter volume of sterile oil is then added. A 10 microliter aliquot of the DNA extract is then added and this brings the buffer and reagents to their final concentrations as stated above.

The reaction mixture is then subjected to the first round of thermocycling as follows: an initial incubation at 94° C. for 7.5 minutes to melt the DNA is followed for 16 cycles, each cycle consisting of 40 seconds at 55° C. for annealing the primers, one minute at 72° C. for extending the primers, and, finally, 40 seconds at 94° C. for remelting. The samples are then transferred to ice before the second round of PCR. Samples can also be stored, if necessary, at 4 or −20° C. for considerable periods of time.

Second Round

The reactions are conducted in 50 microliter volumes with an overlay of 50 microliters of light paraffin oil. The buffer, enzyme, and nucleotide concentrations are identical to the first round of PCR. The only difference is that the concentration of both second round primers LP1 (5'-GCG GCG TGC CTA ATA CAT GC-3') (SEQ ID NO:3) and C (5'-TCA GTT ACA GAC CAG AC-3') (SEQ ID NO:4) is at 500 nanomoles/liter. As with the first round, reagents are made up in 40 microliter volumes, to which 10 microliters of the first round reaction volume are added, bringing the final reagent concentrations to those described for the first round.

The reaction mixture is then subjected to the second round of thermocycling as follows: an initial incubation at 94° C. for five minutes to melt the DNA is followed for 31 cycles, each cycle consisting of 40 seconds at 55° C. for annealing the primers, one minute at 72° C. for extending the primers, and, finally, 40 seconds at 94° C. for remelting.

After the final 94° C. incubation the samples are incubated at 55° C. for 40 seconds for primer annealing, followed by a final extension incubation at 72° C. for ten minutes. Once the second round is complete the amplification products can be detected, preferably by gel electrophoresis.

Further information concerning primer LP1 (5'-GCG GCG TGC CTA ATA CAT GC-3') (SEQ ID NO:3) can be found in N. Klijn et al., *Applied Environmental Microbiology* 57:3390–93 (1991). In that same connection, 16S RNA primers directed against conserved regions of the gene are discussed in D. R. Woese, *Microbiol. Rev.* 51:221–71. Similarly, additional information relating to primer Common (i.e., "C" (5'-TCA GTT ACA GAC CAG AC-3') (SEQ ID NO:4)) can be found in L. J. DiMichele et al., *Journal American Society of Brewing Chemists* 51:63–66 (1993). Information regarding 16S ribosomal RNA sequences of Lactobacillus species, is contained in M. D. Collins et al., *FEMS Microbiol. Lett.* 77:5–12 (1991).

In any case, once the nested PCR amplification stages are complete, the resulting derivative amplified sample is then separated, and any one of a number of detection means can be employed to determine the presence of amplified lactic acid bacterial DNA sequences. Such means include, but are not limited to, hybridization with isotopic or nonisotopically labeled probes in, for example, a dot blot or electrophoretic format.

There are a number of ways to determine whether a probe has hybridized to a DNA sequence contained in a sample. Typically, the probe is labeled in a detectable manner. The target DNA (i.e., the amplified DNA in the PCR-reaction buffer) is bound to a solid support. Hybridization has occurred when the label is present on the solid support. This procedure can be varied, however, and is possible when the target is labeled and the probe is bound to the solid support.

Many methods for labeling nucleic acids, whether probe or target, are known in the art and are suitable for purposes of the present invention. Suitable labels may provide signals detectable by fluorescence, radioactivity, colorimetry, X-ray diffraction or absorption, magnetism, enzymatic activity, and the like. Suitable labels include fluorophores, chromophores, radioactive isotopes, electron-dense reagents, enzymes, and ligands having specific binding partners. Enzymes are typically detected by their activity. For example, horseradish-peroxidase can be detected by its ability to convert diaminobenzidine to a blue pigment.

Amplified nucleic acids can be detected without the use of a probe. The homogeneous assay system requires that amplification occurs in the presence of a detectable DNA binding agent, for example, ethidium bromide. The fluorescence of the amplification mixture increases as the target is amplified and the amount of double-stranded DNA present in the reaction mixture increases.

In an especially preferred form of the present invention, detection is accomplished through separation of the DNA sequences using gel electrophoresis, which is followed by ethidium bromide staining. Under UV light, it is possible to detect an identifiable 750 bp (i.e., double-stranded base pairs) band, if the original sample contained lactic acid bacterial contamination.

The inventors surveyed the reactivity of a number of primers targeted to the small ribosomal DNA genes of beer spoilage lactic acid bacteria. One set, termed LP1 (5'-GCG GCG TGC CTA ATA CAT GC-3') (SEQ ID NO:3) and C (5'-TCA GTT ACA GAC CAG AC-3') (SEQ ID NO:4), reacts almost exclusively with these lactic acid bacteria, including species of Pediococcus, Lactobacillus, and Leuconostoc. Neither yeast nor nonlactic acid bacteria, including both gram-positive and gram-negative species, react with these primers. As little as a single colony forming unit/10 µL can be detected with pure cultures of lactic acid bacteria. The first round amplifies a fragment of DNA that contains within its sequence the primer site for LP1 (5'-GCG GCG TGC CTA ATA CAT GC-3') (SEQ ID NO:3) and the primer site for C (5'-TCA GTT ACA GAC CAG AC-3') (SEQ ID NO:4) for the second round of PCR. Thus, by careful and thoughtful selection of the correct primer sets, PCR can indeed be applied to any target organism or groups of organisms. Furthermore, interference caused by inhibitors present in the sample can easily be overcome using nested PCR.

Extraction of DNA from Fermentation Samples

Materials:
(1) Bench-top microcentrifuge.
(2) Hot plate.
(3) 56° C. water bath.
(4) Micropipetors and tips.
(5) 1.5 mL and 0.5 mL microcentrifuge tubes.
(6) 1.5 mL microcentrifuge tube rack (fitted for boiling water bath.
(7) Instagene Mixture (BioRad).
(8) Vortex genie.
(9) Sterile water.

Separation

The difficulty with analyzing finished beer is that the concentration of bacteria is very low, perhaps only two or three cells per bottle. In this case, the low concentration of bacteria can be captured using antibodies specific to lactic acid bacteria. The antibodies are coupled to magnetic beads that can easily be concentrated using a magnet. The beads, which will have the antibodies and, thus, the bacteria attached to them, can then be used for the nested PCR reaction.

Capture of Lactic Acid Bacteria Using Immunospecific Beads

The bacteria in beer are captured by the addition of 1 mg of antibody-coated magnetic beads to each 100 mL of beer. The sample is then incubated for 30 minutes at ambient temperature with gentle shaking. For convenience, the beer sample can be transferred into two 50 mL aliquots with 0.5 mg of the antibody-coated beads added to each tube. For larger volumes, the appropriate number of tubes can be used. Note that an excess of beads is added to ensure capture of low concentrations of bacteria (each gram of beads contains on the order of $10^{10}$ beads). After the incubation period, the beads are allowed to settle in the tube(s). The beads are then captured using a magnetic tube stand, which concentrates the magnetic beads at the bottom of the tube within 30 seconds. (Note: Magnetic tube stands for 50 mL tubes, the largest currently available, can be purchased from two suppliers: (1) product MPC-1 from Dynal, Lake Success, N.Y. 11042; or (2) product Z5343 from Promega, Madison, Wis. 53711-5899). The beer supernatant is then decanted from each tube with the beads held in place by the magnetic tube stand. The beads are then resuspended in a minimal volume of water and are combined together into a single tube. This tube is then transferred back to the magnetic tube stand to collect the magnetic beads. The beads are then washed twice more with sterile water using the same procedure. The final pellet beads can then be resuspended in the Instagene Mixture for DNA extraction.

Extraction of DNA (1) The 1 mL sample is mixed to ensure the sample is completely suspended and aliquots of this volume are then transferred to 1.5 mL microcentrifuge tubes. The 1.0 mL sample is divided into three aliquots of 200 microliters, two aliquots of 100 microliters, and three aliquots of 50 microliters. The aliquots are then centrifuged at 12,000 rpm for three minutes.

(2) The Instagene Mixture (commercially available from BioRad Laboratories, 2000 Alfred Nobel Drive, Hercules, Calif. 94547) is placed into a 56° C. bath, so that it is equilibrated before addition to the samples.

(3) The tubes are then transferred from the centrifuge to a suitable rack and the supernatants are removed and discarded.

(4) The prewarmed Instagene Mixture bottle is transferred to a magnetic stir plate with the stirring rate set at a pace to suspend the mixture sufficiently. If the mixture is not fully suspended, the proportion of silica beads and extract buffer contained therein will deviate from the optimum, resulting in poor DNA extraction. To each tube, add 200 microliters of the Instagene Mixture.

(5) The tubes are then transferred to the 56° C. bath and incubated for 25 to 45 minutes (~30 minutes is the normal period). During this incubation period, a boiling water bath is prepared.

(6) After 56° C. incubation, the tubes are vortexed vigorously for one minute and then transferred to the boiling water bath for eight minutes.

(7) The tubes are then vortexed for a further eight minutes. The silica beads are then pelleted by centrifugation for three minutes at 12,000 rpm. The supernatants of each (0.150 mL) are transferred to 0.5 mL microcentrifuge tubes. The samples are now ready for amplification by PCR and subsequent analysis.

(8) The tubes can be stored at either 4 or −20° C. The 4° C. storage is adequate for a short term, but if long term storage is desired (>three months), then −20° C. is recommended.

PCR Sample Set-up

The order in which the samples are set up for PCR is important for controlling the incidence of contamination. Owing to the high sensitivity of the technique, cross contamination between samples can occur. Particularly, samples that are known to contain target DNA (i.e., positive controls) can easily contaminate test samples or negative controls. For this reason the Master Mix and oil are added to the tubes and the tubes are capped before the DNA samples are obtained from the refrigerator. In addition, the positive control sample is obtained from the refrigerator after all the test samples and negative controls have been aliquoted.

The following are a number of guiding principles that can help to minimize the occurrence of false positive results.

(1) Intersperse $H_2O$ controls every few samples. This will help to identify cross-contamination, particularly when aliquoting the samples from the first round to the second round.

(2) Change gloves frequently. Latex gloves can be contaminated with samples that contain the target DNA and any incidental contact between the pipet tips and the gloves can result in contamination. A rule of thumb is that if it is suspected that either the tip or the gloves have brushed against a surface that could potentially be contaminated, the gloves and tip should be changed immediately. For example, opening sample tubes can cause aerosols or splashing of the tube contents resulting in contamination of the gloves. Indeed, the formation of aerosols during pipetting dictates the use of pipet tips having cotton plugs as an aerosol barrier.

(3) The Master Mix reagents should not be permitted to come into contact with DNA. Make up the Master Mix aliquots under conditions in which it is impossible to contaminate samples with DNA. Use a disinfected area to make up the solutions and do not allow any DNA extracts in the vicinity. In particular, do not allow any amplified products into the same area, as these are highly efficiently amplified by PCR. For this reason, the PCR Master Mix and the PCR set-up should be conducted in areas different from those used for detection, for example, gel electrophoresis. Note that living microorganisms can also contaminate solutions. They, of course, contain DNA that may be amplified if intact microorganisms are present in the Master Mix. Thus, care must be taken to minimize the presence of microbial suspensions when Master Mix solutions are being prepared or when PCR tubes are being set up. Do not set up a PCR tube while also handling microorganisms. The same area can, of course, be used for PCR work and work with microorganisms, but before engaging in the PCR work, the area must be effectively disinfected.

(4) Disinfect PCR areas frequently. Weekly cleaning of surfaces with bleach will destroy any contaminating DNA. Also, treatment of surfaces with UV radiation will destroy DNA. Using both methods is highly recommended.

Preparation of Master Mix Aliquots
(All Volumes are in Microliters)

| | | | | | | | |
|---|---|---|---|---|---|---|---|
| Number of Aliquots | 5 | 10 | 20 | 100 | 500 | 1000 | 10000 |
| 10X PCR Buffer | 25 | 50 | 100 | 500 | 2500 | 5000 | 50000 |
| dNTP's | 25 | 50 | 100 | 500 | 2500 | 5000 | 50000 |
| Sterile Water | 143.75 | 287.5 | 575 | 2875 | 14375 | 28750 | 287500 |
| Taq | 1.25 | 2.5 | 5 | 25 | 125 | 250 | 2500 |
| Primer 1 | 2.5 | 5 | 10 | 50 | 250 | 500 | 5000 |
| Primer 2 | 2.5 | 5 | 10 | 50 | 250 | 500 | 5000 |

"Primer 1" in the above table is the forward primer and "Primer 2" is the reverse primer. The difference between the first and second round set ups is that the first round primers have a lower concentration than the second round primers. Primer 1 in the first round is NSN10F (5'-AGA GTT TGA TCC TGG CTG AGC-3') (SEQ ID NO:5) and Primer 2 is NSN986R (5'-TGC TCC ACC CGT TGT GCG-3') (SEQ ID NO:6). The second round primers are LP1 (5'-GCG GCG TGC CTA ATA CAT GC-3') (SEQ ID NO:3) and C (5'-TCA GTT ACA GAC CAG AC-3'), respectively.

Nested PCR Protocol

Reagents:

Working volumes of Master Mix containing the desired amounts of enzyme, buffer, and primer are made up on 10-sample sized aliquots from reagent stock solutions. Many 10-sample aliquots are generally made up at the same time and are stored at −20° C. Master Mix for both the first and second rounds of PCR must be made up beforehand.

(1) Sufficient amounts of Master Mix I (first round) and Master Mix II (second round). Note: For every nine samples to be analyzed (including controls), ten sample volumes of Master Mix are needed, i.e., a 10 percent excess volume of Master Mix is needed to account for losses during pipetting.

(2) Instagene Mixture DNA Extracts.

(3) Positive Control DNA (Purified B12 DNA).

First Round of PCR:

(1) Remove Master Mix I from the freezer and thaw in the fumehood.

(2) Start the thermocycler on the nested program NSTD1 and pause at step 1 (94° C.).

(3) Set up 0.5 mL microcentrifuge tubes in appropriate tube holder.

(4) Add 40 microliters of Master Mix I to each of the tubes followed by 40 microliters mineral oil.

(5) Cap all of the tubes and label each with an indelible marker.

(6) Add 10 microliters of water to the negative control sample and cap the tube.

(7) Aliquot 10 microliters of the DNA extracts into the designated PCR tubes.

(8) Remove the DNA positive control from the refrigerator and add ten microliters to the corresponding PCR tube.

(9) Place the tubes in thermocyclers and release the program from pause mode.

Second Round of PCR:

(10) Seventy minutes after starting the round, obtain the appropriate volume of Master Mix II from the freezer and thaw it in the fumehood.

(11) Set up the 0.5 mL microcentrifuge tubes in the tube holder, including an extra water negative control sample for round 2.

(12) Add 40 microliters of Master Mix II, followed by 40 microliters of sterile oil to each tube, taking care that the labels distinguish between samples from round 1 and round 2.

(13) Add 10 microliters of sterile water to the round 2 negative control tube.

(14) When the thermocycler completes round 1 of PCR, pause the machine at the round 2 hotstart, step 6.

(15) Transfer the round 1 tubes to ice and place in the fumehood.

(16) Aliquot 10 microliters of each round 1 tube to its corresponding round 2 tube, changing gloves after every six tubes.

(17) Place the round 2 tubes in the thermocycler and release the program from the pause mode.

(18) Store both the round 1 samples and the round 2 samples at 4° C. until needed for analysis.

Agarose Gel Electrophoresis

Materials:

(1) Agarose. Although most biological manufacturers offer comparable PCR grade agarose, Trevigel® brand is preferred in the practice of the present invention. Owing to its increased stability and high optical clarity, lower percentage gels, lower gel volumes, lower amounts of ethidium bromide, and lower sample volumes can be used, thereby reducing costs.

(2) TAE Buffer. TrisAcetate-EDTA buffer is prepared fresh from a 50× TAE stock. After dilution, two microliters of a 10 mg/mL solution of ethidium bromide are added to one liter of 1× TAE. (Final concentration=0.02 μg/mL).

Add agarose to 1× TAE buffer containing 0.02 μg/mL ethidium bromide. For best results, the buffer used for gel casting should be from the same batch as for electrophoresis. Shake the flask thoroughly to ensure that the gel is completely suspended and contains no clumps. Weigh the flask on a balance and microwave at high power until completely dissolved, taking care that the flask does not boil over. Weigh the flask again and return any lost weight by adding sterile water. Then incubate the flask at 50 to 55° C. for ten minutes to allow bubbles to disperse and to cool the gel below 60° C. If the agarose is too hot, the gel holder may crack. Place the gel in the refrigerator for 15 minutes and then add to the electrophoresis apparatus. Do not remove the combs until the gel is submerged and in place in order to prevent tearing of the gel or destruction of the wells upon removal. After removing the combs, remove any fragments of agarose from within the wells.

Set up a series of microdroplets of 5× loading buffer on Parafilm (about two to three microliters per droplet). Mix an aliquot of the PCR sample with one droplet and swirl to allow the oil to adhere to the waxy surface of the Parafilm. Carefully add to the well, but fill the well only about three-fourths full. For most gels, four to five microliters of sample are sufficient. Greater filling leads to cross-contamination and possible artefactual bands. Use a fresh pipet tip for every sample. Note: The small droplets of loading buffer evaporate very quickly. With a large number of samples, additional fresh droplets may be needed.

The following procedures and precautions will help to ensure accurate and precise results.

(1) Make sure the glassware is scrupulously clean, dust free, and autoclaved.

(2) Replace evaporated water by taring the agarose/gel/buffer mixtures before boiling in the microwave.

(3) Thinner teeth on the combs result in sharper bands.

(4) Do not overload the gel, about 75 percent capacity is optimal.

(5) Resolution is improved with longer gels, cooler temperatures, and lower voltages (i.e., running speeds).

(6) The use of thinner gels improves heat transfer and increases the sensitivity of detection.

(7) Use sucrose or Ficoll, not glycerol, for loading buffer.

(8) Make sure the gels are level. A slanted surface can dramatically alter electrophoretic separation and resolution.

(9) Clean all plastic ware, including the comb teeth, with water before use. No salt or gel residue should be visible.

(10) Make sure the melted agarose has no air bubbles before pouring into the gel mould. If any form during pouring, remove, using a pipet tip.

(11) Remove contaminating fluid from the well surface by gently adding a small amount of buffer.

(12) Make the gel between 4 and 6 mm thick.

The foregoing description of the preferred embodiments of the invention has been presented for purposes of illustration and description. It is not intended to be exhaustive or to limit the invention to the precise form disclosed, and obviously many modifications and variations are possible in light of the above teaching. Such modifications and variations that may be apparent to a person skilled in the art are intended to be included within the scope of this invention as defined by the accompanying claims.

---

What is claimed is:

1. A method for the rapid, high-sensitivity detection of lactic acid bacteria in a finished beer sample, wherein the method consists essentially of the steps of:

aseptically sampling a finished beer;

separating any bacteria in the sample by means comprising beads having antibodies attached thereto;

extracting DNA from the separated bacteria;

subjecting the extracted DNA to a nested polymerase chain reaction, said reaction comprising:

enzymatically amplifying a target sequence of bacterial 16S rDNA using a pair of 16S rDNA specific primers to produce a first amplified sample; and further enzymatically amplifying a product sequence from said first amplified sample using a pair of lactic acid bacteria specific primers comprising LP1 (5'-GCG GCG TGC CTA ATA CAT GC-3') (SEQ ID NO: 3) and C (5'-TCA GTT ACA GAC CAG AC-3') (SEQ ID NO: 4) to produce a second amplified sample; and then subjecting the second amplified sample to separation and staining to detectably segregate an identifiable band comprising amplification products associated with said lactic acid bacteria, wherein detection of said identifiable band comprising amplification products is indicative of the presence of lactic acid bacteria.

2. The method of claim 1 wherein the beads are magnetic beads.

3. The method of claim 1 wherein the lactic acid bacteria to be detected are selected from the group consisting of:

Pediococcus damnosus;
Lactobacillus brevis (varlindneri);
Lactobacillus plantarum;
Pediococcus damnosus (cerevisiae);
Lactobacillus acidophilus;
Lactobacillus bulgaricus;
Leuconostoc mesenteroides;
Lactobacillus helveticus;
Pediococcus inopinatus;
Lactobacillus fermentum;
Lactobacillus casei alactosus;
Pediococcus halophilus;
Lactobacillus delbrueckii;
Leuconostoc mesenteroides subsp. dextrinicum;
Lactobacillus buchneri;
Lactobacillus casei varcasei;
Pediococcus intermedius;
Pediococcus parvulus;
Pediococcus dextrinicus; and
Streptococcus lactis.

4. The method of claim 1 wherein the nested polymerase chain reaction is carried out in the presence of Taq DNA polymerase.

5. The method of claim 1 wherein the second amplified sample is separated by gel electrophoresis.

6. The method of claim 1 wherein the staining step employs ethidium bromide.

7. The method of claim 5 wherein the staining step employs ethidium bromide.

8. The method of claim 1 wherein the means for separating the bacteria in the sample further comprises a ligand that can bind to bacteria.

9. A method for the rapid, high-sensitivity detection of lactic acid bacteria in a finished beer sample, wherein the method consists essentially of the steps of:

aseptically sampling a finished beer;

separating any bacteria in the sample by means comprising magnetic beads having antibodies attached thereto;

extracting DNA from the separated bacteria;

subjecting the extracted DNA to a nested polymerase chain reaction, said reaction comprising:

enzymatically amplifying a target sequence of bacterial 16S rDNA using a pair of 16S rDNA specific primers, NSN10F (5'-AGA GTT TGA TCC TGG CTG AGC-3') (SEQ ID NO: 5) and NSN986R (5'-TGC TCC ACC CGT TGT GCG-3') (SEQ ID NO: 6), to produce a first amplified sample; and further enzymatically amplifying a product sequence from said first amplified sample using a pair of lactic acid bacteria specific primers comprising LP1 (5'-GCG GCG TGC CTA ATA CAT GC-3') (SEQ ID NO: 3) and C (5'-TCA GTT ACA GAC CAG AC-3') (SEQ ID NO:4) to produce a second amplified sample; and then subjecting the second amplified sample to separation by gel electrophoresis and staining with ethidium bromide to detectably segregate an identifiable band comprising amplification products associated with said lactic acid bacteria, wherein detection of said identifiable band comprising amplification products is indicative of the presence of lactic acid bacteria.

10. The method of claim 9 wherein the means for separating the bacteria in the sample further comprises a ligand that can bind to bacteria.

11. The method of claim 9 wherein the lactic acid bacteria to be detected are selected from the group consisting of:

Pediococcus damnosus;
Lactobacillus brevis (varlindneri);
Lactobacillus plantarum;
Pediococcus damnosus (cerevisiae);
Lactobacillus acidophilus;
Lactobacillus bulgaricus;
Leuconostoc mesenteroides;
Lactobacillus helveticus;
Pediococcus inopinatus;
Lactobacillus fermentum;
Lactobacillus casei alactosus;
Pediococcus halophilus;
Lactobacillus delbrueckii;
Leuconostoc mesenteroides subsp. dextrinicum;
Lactobacillus buchneri;
Lactobacillus casei varcasei;
Pediococcus intermedius;
Pediococcus parvulus;
Pediococcus dextrinicus; and
Streptococcus lactis.

12. The method of claim 11 wherein the means for separating the bacteria in the sample further comprises a ligand that can bind to bacteria.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide"

(xi) SEQUENCE DESCRIPTION: SEQ ID NO:1:

TGTGGTGGCG ATAGCCTGAA                                      20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide"

(xi) SEQUENCE DESCRIPTION: SEQ ID NO:2:

GCGTGGCAAC GTCCTATCCT                                      20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:3:

GCGGCGTGCC TAATACATGC                                20

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:4:

TCAGTTACAG ACCAGAC                                   17

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:5:

AGAGTTTGAT CCTGGCTGAG C                             21

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:6:

TGCTCCACCC GTTGTGCG                                  18